United States Patent [19]

Timm

[11] Patent Number: 4,515,166
[45] Date of Patent: May 7, 1985

[54] NOCTURNAL PENILE TUMESCENCE AND RIGIDITY MONITOR

[75] Inventor: Gerald W. Timm, Minneapolis, Minn.

[73] Assignee: Dacomed Corporation, Minneapolis, Minn.

[21] Appl. No.: 503,872

[22] Filed: Jun. 13, 1983

[51] Int. Cl.³ .............................................. A61B 5/00
[52] U.S. Cl. ..................................... 128/694; 128/774
[58] Field of Search ...................... 128/694, 774, 782; 33/174 D

[56] References Cited

U.S. PATENT DOCUMENTS

| | | | |
|---|---|---|---|
| 4,103,678 | 8/1978 | Karacan et al. | 128/2.05 |
| 4,274,424 | 6/1981 | Kimura et al. | 128/686 |
| 4,428,385 | 1/1984 | Morales | 128/774 |
| 4,469,108 | 9/1984 | Goldstein | 128/694 |

OTHER PUBLICATIONS

"A Simple and Inexpensive Transducer for Quantative Measurements of Penile Erection During Sleep, Behavior Research Methods and Instrumentation," vol. 1, pp. 251-252, 1979, Author: Ismet Karacan.
"Some Characteristics of Nocturnal Penile Tumescence in Young Adults", Archives General Psychiatry, vol. 26, pp. 351-356, 1972, Author: Ismet Karacan.
"Sleep Related Penile Tumescence as a Function of Age", American Journal of Psychiatry, vol. 132, pp. 932-937, Sep. 1975, Author: Ismet Karacan.
"Nocturnal Penile Tumescence Monitoring with Stamps", Urology, vol. 15, pp. 171-172, 1980, authors: John M. Barry, MD.D, Bruce Blank, M.D., and Michael Boileau, M.D.
"Normative Studies on a New Device for Evaluation of Nocturnal Penile Tumescence," Notice of American Urological Association, Inc. 77th Annual Meeting, Presented by Dr. Alvaro Morales.
Brochure for Erectiometer, manufacturer: Walter Koss OHG.
"The Role of the Sleep Laboratory in Diagnosis and Treatment of Impotence," In: *Sleep Disorders: Diagnosis and Treatment*, Ed. by R. L. Williams and I. Karacan, Chapter 14, pp. 365-366, 1978.
Brochure for Rigidimeter, (France).

*Primary Examiner*—Kyle L. Howell
*Assistant Examiner*—John C. Hanley
*Attorney, Agent, or Firm*—Merchant, Gould, Smith, Edell, Welter & Schmidt

[57] ABSTRACT

A penile rigidity and tumescence monitor apparatus is disclosed. The monitor apparatus includes a transducer apparatus (20) for providing output signals indicative of penile rigidity and tumescence throughout a penile tumescence event. A control apparatus (22) is operatively interconnected to the transducer apparatus (20) for providing control thereover. The control apparatus (22) also provides for acquisition and storage of penile rigidity and tumescence data represented by the output signals received from the transducer apparatus (20).

19 Claims, 3 Drawing Figures

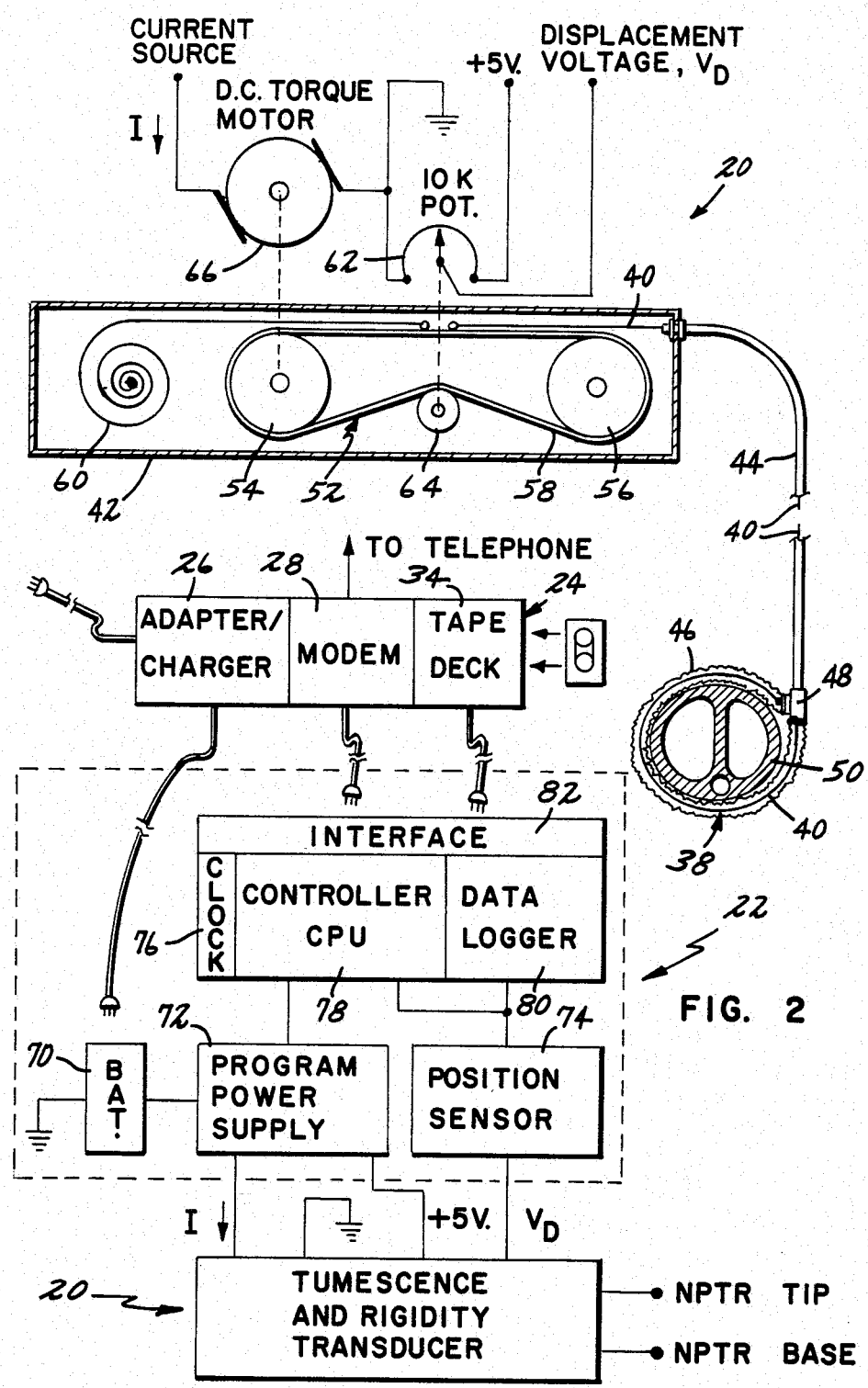

NOCTURNAL PENILE TUMESCENCE AND RIGIDITY MONITOR

BACKGROUND OF THE INVENTION

The present invention relates to a nocturnal penile tumescence and rigidity monitor. More particularly, the present invention relates to a nocturnal penile tumescence and rigidity monitor which, in addition to providing for continuous monitoring of tumescence, provides a record of the rigidity attained at predetermined intervals during a penile tumescence event. Accordingly, the present invention provides an indication of the duration of rigidity during the penile tumescent event.

As previously indicated in pending applications, Ser. No. 318,373, filed Nov. 5, 1981, and Ser. No. 378,709 filed May 17, 1982, studies have shown that men with psychogenic impotence generally have normal sleep erections, whereas men with organic impotence have sleep erections that correspond to their impaired wake performance. Such studies have alerted the scientific community of the potential usefulness of nocturnal penile tumescence monitoring in the differential diagnosis of sexual impotence. As a result of the recognition that nocturnal penile tumescence monitoring can be of assistance in diagnosing male erectile impotence, various types of devices and techniques for conducting such monitoring have been developed.

In an article entitled "A Simple and Inexpensive Transducer for Quantitative Measurement of Penile Erection During Sleep", Behavior Research Methods and Instrumentation, Volume 1, pages 251–252, 1969, Ismet Karacan describes a mercury strain-gauge transducer for detecting penile erection. The transducer device is an elastomeric mercury filled tube which is suitably connected to a wheatstone bridge and amplifier circuit for recording purposes. As the transducer changes size during penile erection, its electrical resistance changes thereby causing the amplified output from the wheatstone bridge to change. The amplified changes in the output are recorded enabling penile activity to be recorded.

In an article entitled "Some Characteristics of Nocturnal Penile Tumescence in Young Adults", Archives General Psychiatry, Volume 26, pages 351–356, 1972, Ismet Karacan et al. describes the normative characteristics of nocturnal penile tumescence (NPT) in a group of 20 to 26 year old men who were measured during continuous all-night recording utilizing the mercury strain-gauge transducer.

Additionally, a number of devices and procedures for monitoring penile tumescence during sleep are noted and referenced in an article entitled "Sleep Related Penile Tumescence as a Function of Age", American Journal of Psychiatry, Volume 132, page 9, September 1975.

In U.S. Pat. No. 4,103,678 issued to Ismet Karacan et al. an apparatus is disclosed for recording minute variations in mercury strain-gauge transducers positioned at the base and the tip of the penis.

The above-referenced materials relate to nocturnal penile tumescence activity and not to the measurement of penile rigidity or hardness during the tumescent event. While it is recognized that nocturnal penile tumescence activity is important to the evaluation of organic impotence, another significant aspect in evaluating organic impotence is the quality or rigidity/hardness achieved during the penile tumescent event.

The mercury strain-gauges described by Ismet Karacan provide a measurement of the changes in penile size during a penile tumescent event by changing their impedance as they expand and contract with variations in the penis circumference. The mercury strain-gauges do not, however, provide for measurement of penile rigidity or hardness since the strain-gauges are very elastomeric. A very slight amount of force will fully expand the strain-gauges just as would a larger amount of force.

In addition, the mercury strain-gauge necessitates a rather elaborate monitoring mechanism. The monitoring normally must occur in a health care facility under the supervision of trained professionals. This requires that the patient may be in the health care facility overnight and be subjected to fairly elaborate testing. In addition to creating a substantial imposition on the patient's daily routine, substantial expense is associated with the support facilities and support personnel required to obtain valid test results.

In an article entitled "Nocturnal Penile Tumescence Monitoring with Stamps", Urology, Volume 15, pages 171–172, 1980, a stamp technique is described for detecting complete nocturnal erection for the evaluation of impotence. In this technique, a strip of four postage type stamps is wrapped snuggly around the penis, and the overlapping stamp is moistened to provide a one half to one stamp overlapping seal. The nocturnal penile tumescent stamps, each one and one quarter by one inch, are made on ten by eight inch sheets of paper having water base glue on the opposite side. The patients or subjects are able to perform the evaluations at home rather than go to the hospital, resulting in substantial financial savings. The article indicated that three nights of inhospital nocturnal penile tumescence testing including direct observation of indicated erections and physicians professional fee, currently cost roughly $500. The stamp testing method costs 30 cents for three nights of outpatient testing.

The stamps have a tendency to release after being wetted and stuck together. In addition, the force required to break the perforations between adjacent stamps varies substantially. Thus, the above described stamp technique does not provide a method for accurately detecting a predetermined penile rigidity or hardness.

In Ser. Nos. 318,373 and 378,709, there is disclosed threshold penile rigidity measuring devices which provide for accurate measurement of a predetermined penile rigidity during a penis tumescence event. However, while these devices provide a safe, simple, accurate and reproducible test which can be used at home to provide a very effective tool in the evaluation of impotence, they do not provide for measuring and recording of penile rigidity at various times throughout the tumescence events and accordingly do not provide any record or indication of the duration which the rigidity is maintained. These devices included a ring-like structure having an attachment mechanism for releasably attaching the ring-like structure to a penis. Associated with the ring-like structure is an apparatus for detecting a predetermined force in the penile tumescent event.

The present invention overcomes these and many other problems associated with currently available devices.

SUMMARY OF THE INVENTION

The present invention relates to a penile rigidity and tumescence monitor apparatus comprising transducer means for providing output signals indicative of penile rigidity and tumescence. Operatively associated with the transducer means is control means for providing control of the transducer means. The control means provides further for the acquisition of the output signals and storage of penile rigidity and tumescence data represented by said output signals.

In one embodiment of the present invention, the apparatus includes a portable housing having an elongated, non-distensible, flexible member extending therefrom. The elongated member is constructed and arranged for forming a loop-like portion at a first end. The loop-like portion is adapted for releasably encircling a penis about the circumference thereof. The elongated member is slideably enclosed within a flexible, non-compressible conduit between the loop-like portion and the housing, the non-compressible conduit being suitably attached to the housing. The preferred embodiment further includes biasing means positioned within the housing and operatively interconnected to a second end of the elongated member within the housing for maintaining the elongated member in a tensioned condition. The elongated member is further slideably enclosed in a collapsible, soft sheath along the loop-like portion whereby changes in the penile circumference result in a displacement of the elongated member within the conduit and the sheath. The apparatus further includes means operatively interconnected to the elongated member for sensing displacement of the elongated member in response to changes in penile circumference or tumescent activity, the sensing means providing an output signal indicative of the displacement and accordingly the change in penile circumference. Additionally, the preferred embodiment includes means operatively interconnected to the elongated member for exerting a predetermined force on the elongated member by pulling on the elongated member, the force tending to reduce the size of the loop-like portion. The sensing means senses displacement of the elongated member caused by exertion of the above-mentioned force and provides an output signal indicative of the displacement and accordingly the penile rigidity, as the penile rigidity will affect the amount of displacement which occurs when the force is exerted on the elongated member. Control means operatively interconnected to the sensing means provides for acquiring the output signals and storing penile rigidity and tumescence data represented by the output signals, the control means also providing for activation of the force means at predetermined intervals.

In the preferred embodiment, the biasing means is a constant force spring attached to the chain or belt of a sprocket drive mechanism. The elongated member is also suitably attached to the chain or belt of the sprocket drive. The constant force spring maintains a slight tension in the cable, sufficient to overcome bearing and cable/conduit friction, but not enough to compress a flaccid penis.

In yet another embodiments of the invention, the constant force spring might be replaced by periodically exerting a force on the elongated member sufficient to place the elongated member in tension.

In one embodiment of the present invention, the sensing means includes an angular potentiometer operatively interconnected to an idler sprocket of the sprocket drive mechanism. Accordingly, as the elongated member is displaced, the potentiometer wiper voltage changes in direct relation to the displacement of the elongated member.

The predetermined force means in one embodiment of the present invention includes a torque motor operatively interconnected to a drive sprocket of the sprocket drive mechanism. By passing a fixed, predetermined current through the torque motor, a calibrated force is exerted on the loop like portion encircling the penis. The elongated member displacement in response to this calibrated force is a function of the compressibility or rigidity of the penis.

In still another embodiment of the present invention, the transducer means monitors penile tumescence only.

In yet other embodiments of the present invention, a second transducer might be mounted within the housing to permit concurrent testing of penile base and tip portion rigidities.

The present invention is particularly advantageous in that in the preferred embodiment it provides for continuous monitoring of penile tumescence and further provides for measurement of penile rigidity throughout the penile tumescent events. Accordingly, the present invention provides a trace or record of the tumescence and rigidity at various times throughout the penile tumescent events and provides for measurement of rigidity duration.

Furthermore, the present invention is ambulatory, enabling its use at a remote site, such as a patient's home, away from the hospital. Accordingly, the testing or screening can be performed with very little impact on a person's daily routine or schedule by not requiring that the subject stay overnight in a health care facility. Additionally, the present invention in its simplest form requires little support equipment, special facilities or support personnel. Thus, the present invention provides a simple but effective and accurate technique for monitoring penile rigidity and tumescence during penile tumescent events while a person is sleeping at home. Additionally, since there is no tape or other complicated attachments to the body, there is no discomfort to the patient, thereby allowing the patient to attain a restful night's sleep while the testing is performed.

In a preferred embodiment, the present invention further includes a control processor unit programmed with an algorithm so as to be capable of detecting patient tampering thereby greatly increasing the integrity of the data obtained.

In yet other embodiments of the present invention, the penile tumescence and rigidity monitor includes a data communications link capability so as to permit repetitive nightly testing at home (or at a remote, familiar site) without necessitating personally bringing the collected data to the hospital/clinic for interpretation.

These and various other advantages and features of novelty which characterize the invention are pointed out with particularity in the claims annexed hereto and forming a part hereof. However, for a better understanding of the invention, its advantages, and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views, FIG. 1 is a diagrammatic view of a preferred embodiment of a tumescence and rigidity transducer apparatus in accordance with the principles of the present invention;

FIG. 2 is a diagramatic representation of an ambulatory control apparatus and data logger of a preferred embodiment of the present invention interconnected to the transducer apparatus shown in FIG. 1; and, FIG. 3 is an overall diagramatic view of various data communications between the transducer/control apparatus and a programmable scanner apparatus and its associated peripherals.

DETAILED DESCRIPTION OF A PREFERRED EMBODIMENT OF THE INVENTION

Figure 3:
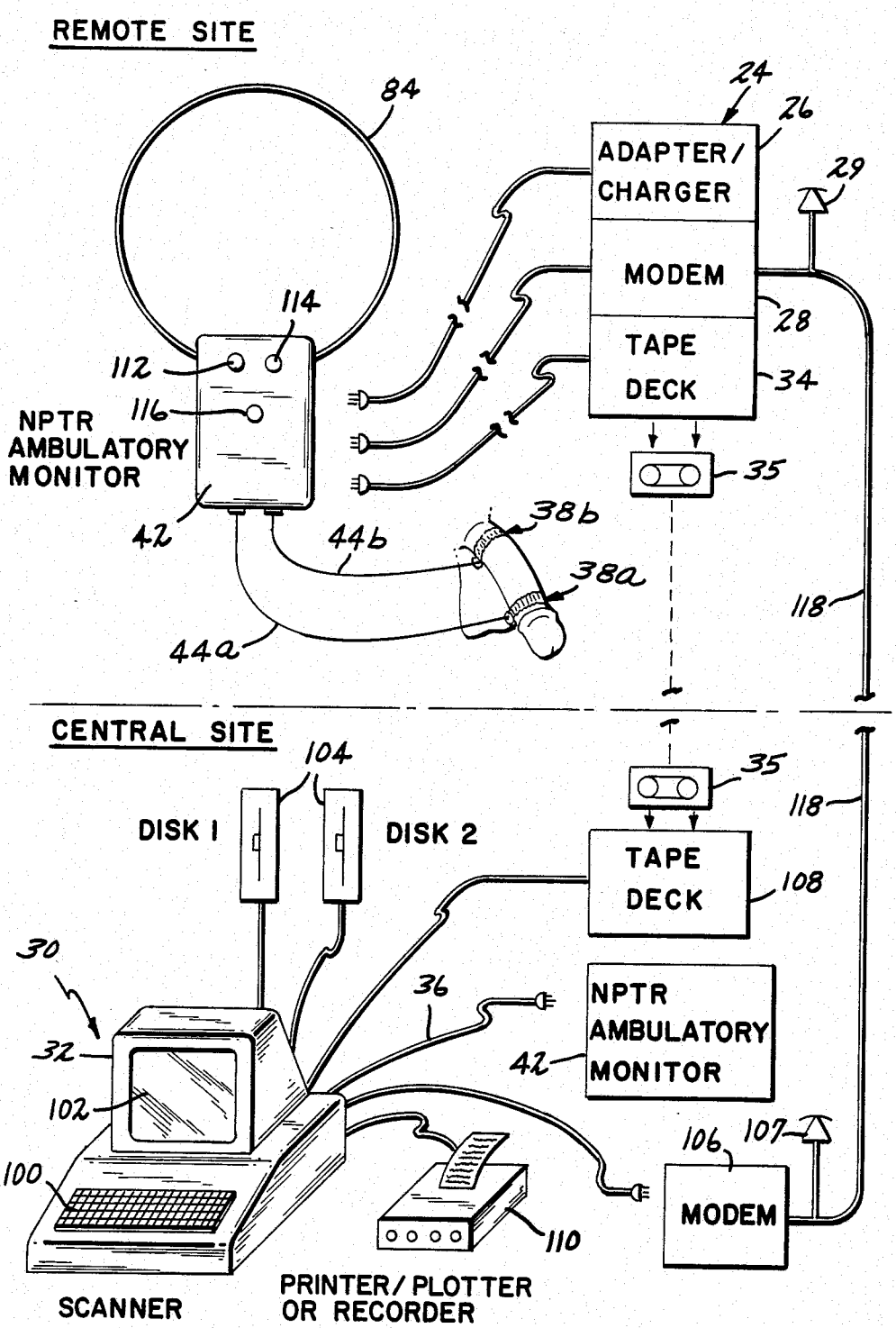

Referring now to the drawings, there is shown diagramatically in FIG. 1 a transducer apparatus of the nocturnal penile rigidity and tumescence monitor apparatus of the present invention for measuring penile tumescence and rigidity, the transducer apparatus generally referred to by the reference numeral 20. As illustrated in FIG. 2, the transducer apparatus 20 is operatively interconnected to a control apparatus 22 providing for control over the transducer apparatus functions and for the logging or storage of penile tumescence or rigidity data collected by the transducer apparatus 20. The transducer apparatus 20 and the control apparatus 22 make up the ambulatory nocturnal penile tumescence monitor of the present invention. Additionally, as further illustrated in FIG. 2, the preferred embodiment of the control apparatus 22 may be operatively interconnected to a peripheral housing 24 preferably including an adapter/charger 26 enabling the control apparatus 22 to be recharged by plugging the adapter 26 into a conventional 110 volt alternating current outlet. Additionally, in the preferred embodiment, the peripheral housing is shown as including a modem 28 enabling transfer of data from the nocturnal penile rigidity and tumescence monitor apparatus to a remotely located system scanner 30 preferably including a programmable central processing unit such as a personal computer 32 as generally illustrated in FIG. 3. Additionally, the peripheral housing might also include a tape deck 34 enabling data to be recorded on a cassette and then handcarried to the central system scanner station. As illustrated in FIG. 3, the penile rigidity and tumescence monitor apparatus might also include a direct connect between the control apparatus 22 and the system scanner 30 as generally illustrated by the direct connection 36.

More particularly, as illustrated in FIG. 1, the transducer apparatus 20 of the preferred embodiment includes a nylon coated, woven, non-distensible cable or elongated member 40 which extends from a housing 42. The elongated member is slideably enclosed within a flexible, non compressible conduit and a soft, collapsible fabric loop sheath near a first end thereof. The flexible elongated member 40 may be looped back on itself and connected to the conduit 44 by a force limit, snap coupling apparatus 48, thereby enabling the formation of a loop-like structure 38 for positioning around the circumference of a penis 50.

Preferably the force limit, snap coupling 48 is configured such that upon exertion of a predetermined amount of force, it will release, thereby preventing any injury to the penis. The snap coupling 48 might be configured similar to the snap elements disclosed in Ser. No. 318,373, filed Nov. 5, 1981.

Mounted inside of the housing 42 is a sprocket chain/belt drive 52, including a drive sprocket 54 and an idler sprocket 56. The elongated member 40 is interconnected at an end thereof to a chain or belt 58 of the sprocket drive assembly 52.

Additionally, interconnected to the chain or belt 58 is a constant force spring apparatus 60 which continually maintains a slight tension in the elongated member 40, sufficient to overcome bearing friction of the sprocket drive assembly 52 and cable/conduit friction such that the diameter of the loop-like portion 38 will reflect the circumference of the penis 50, but not enough to compress a flaccid penis. Accordingly, any change in penile circumference occurring during a tumescent event will result in the elongated member 40 being displaced and correspondingly displacement of the chain or belt 58 of the sprocket drive assembly 52.

An angular potentiometer 62 is attached to the sprocket drive assembly 52 by an idler sprocket 64. Preferably, the potentiometer 62 is a 10K precision device with a +5 volt reference voltage. Any displacement of the elongated member 40 caused by changing penile circumference, results in a change in the potentiometer wiper voltage in direct relation to the elongated member's displacement. Accordingly, the potentiometer 62 provides a continuous readout of the tumescence activity.

Also operatively interconnected to the drive sprocket 54 of the sprocket drive assembly 52, is a DC torque motor 66. In the preferred embodiment shown, the torque motor 66 includes a 0 to 5 amp variable direct current supply. By passing a fixed, known current through the torque motor when tumescence occurs, a calibration force can be exerted on the loop-like portion of the elongated member 40 circling the penis. The resultant cable displacement in response to this calibrated force is a function of the compressibility or rigidity of the penis. By repetitively cycling the motor current at timely intervals, a regular sampling of penile rigidity attained during a penile tumescent event is obtained. The torque motor 66 might be activated at more frequent intervals so as to apply a force sufficient to place the cable 40 in tension thereby doing away with the need for the constant force spring 60.

The outputs of the transducer apparatus 20 are the DC motor current representative of the motor, torque developed, and the potentiometer wiper voltage representing loop displacement and penile circumference change.

It will be appreciated that while in the preferred embodiment a constant force spring is utilized to continually maintain the elongated member 40 in a slightly tension state, alternate methods in keeping within the principals of the present invention might be utilized to place the elongated member under tension. Indeed, in some embodiments, the tensioning function might be provided by the torque motor 66 or other motor apparatus wherein the motor would be periodically activated at a somewhat frequent rate to periodically apply a tensioning force through the elogated member 40 and correspondingly placed elongated member 40 under tension, thereby doing away with the necessity of the constant force spring 60. Accordingly, the loop-like portion 38 would be periodically tightened to reflect the circumference of the penis 50.

Additionally, it will be appreciated that still other methods in keeping within the principals of the present invention might be utilized to monitor displacement of the elongated member 40. In one embodiment of the present invention, the angular potentiometer 62 might be suitably interconnected to a pully on the drive shaft on the torque motor 66 instead of the sprocket chain/belt drive 52. Accordingly, the angular potentiometer would detect angular displacement of the drive shaft and accordingly displacement of elongated member 40.

In yet another embodiment, the torque motor 66 and the sprocket drive 52 might be replaced by a linear drive apparatus. A shaft encoder might then be utilized in conjunction with a linear potentiometer to monitor displacement of the elongated member 40. Various other embodiments of the drive apparatus and sensor apparatus might be utilized in keeping within the principals of the present invention.

Furthermore, it will be appreciated that the present invention might be utilized without the penile rigidity monitor function. For example, in certain applications a transducer might be utilized without the DC torque motor 66 or suitable apparatus for periodically applying the calibration force. While still capable of monitoring penile tumescence, the transducer would no longer monitor rigidity. In addition, a transducer mounted in a separate housing might be utilized for monitoring the penile rigidity.

A second transducer may also be mounted in the same housing 42 to permit concurrent testing of penile base and tip portion rigidities as illustrated by 38(b) and 38(a) in FIG. 3.

In use, the end of the elongated member is positioned around the circumference of the penis and the snap coupling 48 is engaged, so as to form the annular loop-like portion 38 thereabout. The constant force spring apparatus 60 maintains a slight tension in the elongated member 40 sufficient to overcome any resistence in the sprocket drive apparatus 52 and cable/conduit friction, but not sufficient to compress a flaccid penis. As the penile circumference changes, the potentiometer wiper voltage changes in direct relation to displacement of the elongated member 40. A fixed, preset current is passed at predetermined intervals through the torque motor 66 when tumescence occurs, thereby exerting a calibrated force on the cable loop 38 encircling the penis. The cable displacement in response to this calibrated force is a function of the compressibility or rigidity of the penis. Repetitive cycling of the motor current at timely intervals provides a regular sampling of penile rigidity attained during a penile tumescence event.

As illustrated in FIG. 2, the control apparatus 22 is operatively interconnected to the transducer apparatus 20 to provide a 0 to 5 amp variable direct current supply to the torque motor 66 and a +5 volt reference voltage for the potentiometer 62. As illustrated in FIG. 2, the control apparatus 22 includes a DC battery 70, a power supply 72, a position sensor 74, and an electronic control unit including an internal clock 76, a programmable central processing unit 78, a data logger or memory unit 80, and an interface unit 82. The battery 70 provides the power for the power supply 72 which in turn provides the direct current to the torque motor 66 and the +5 volt reference voltage for the potentiometer. The position sensor 74 senses the potentiometer wiper voltage indicative of loop displacement and penile circumference change. The internal clock 76 is utilized to determine the time and date that various events occur while the central processor unit 78 provides for control over the power supply 72 and the storage of penile rigidity and tumescence data in conjunction with the data logger 80. The interface unit 82 enables interface communications with the modem 28 and/or the tape deck 34 and any other peripheral equipment as required. Accordingly, the control apparatus 22 performs all transducer apparatus control, data acquisition and storage, and peripheral interface communications.

The transducer apparatus 20 and the control apparatus 22 are preferably contained within the same portable mounting frame. Additionally, the mounting frame or housing 42 is configured such that the nocturnal penile tumescence and rigidity monitor is ambulatory in that it performs data acquisition of all specified physiological inputs while belted or strapped to the patient. A possible configuration is illustrated in FIG. 3, wherein a belt 84 is illustrated as being attached to the housing containing both the transducer apparatus 20 and the control apparatus 22. In this embodiment, a second transducer is mounted within the housing 42 to permit concurrent testing of penile base and tip portion rigidities.

The operation of a preferred embodiment of the control apparatus 22 is as follows:

1. Penile Loop(s) are comfortably fitted at the base (and at the tip) of the penis, and a base line circumference measurement performed.
2. The circumference of the penis is checked every three seconds with the last ten data points (adjustable number of data points) stored in a scratchpad memory.
3. If the circumference increases more than 2 mm (adjustable set point), store the ten data points and subsequent data points in the data logger CMOS RAM (or cassette or bubble or other non-volatile) memory together with the date and time of beginning storage.
4. If the reading is greater than 5 mm (adjustable set point), then turn the torque motor 66 on for 5 seconds (adjustable period and current), and change the sample interval to one second.
5. If the cable displaces less than 3 mm (adjustable set point), indicating a hard penis, sound the buzzer (optional accessory).
6. As long as the tumescence change exceeds 5 mm (or other preset value), repeat step 4 every 3 minutes (adjustable interval).
7. When the reading again falls below 2 mm (or preset value), store time and date and return system to scratchpad store mode as described in step 2.
8. Once an hour, if no tumescence is occurring, a motor cycle as described in step 4 is run, storing also the time and date.

As illustrated in FIG. 3, the nocturnal penile rigidity and tumescence monitor apparatus is utilized in conjunction with a system scanner 30 which is based around a programmable processor such as a personal computer. The system scanner 30 enables the setting of adjustable parameters on the control apparatus 22, provides for analysis of penile rigidity and tumescence data, and provides for support and hard copy print out. It is anticipated that the system scanner 30 will reside at the clinic or other central site and collect the incoming data from various remote patient sites.

Preferably the personal computer 32 is user friendly with extensive use of menus on a CRT to provide operator instruction and guidance. Preferably, the system scanner with its personal computer 32 and various peripheral equipment will provide the following functions:

1. Monitor initialization, including preparation for patient use, self-testing, entering of patient name, entering of patient I.D., updating of the date/time, entering of the monitor apparatus serial number, presetting all adjustable values utilized by the algorithm programmed into the control apparatus 22.

2. Calibration of the nocturnal penile and tumescence rigidity monitor apparatus, including recording the data together with the time and date obtained by running one torque motor cycle after fitting a loop to a patient's penis.

3. Down-loading of nocturnal penile tumescence and rigidity monitor data from the control apparatus memory (random access memory (RAM)), the tape deck, and/or the modem which would automatically retrieve session data stored in the control apparatus 22 or the tape unit 34.

4. Data analysis and print-out including analyzing and constructing in usable form for storage and hard copy print-out, penile rigidity and tumescence data of a session or a singular event analysis. Preferably, optional outputs available from this function would include one or all of the following:
   (a) 2D graphic (CRT or hard copy) output for time versus tumescence/rigidity plots.
   (b) 3D graphic (CRT or hard copy) output of time versus tumescence versus rigidity plots for singular events or entire sessions.
   (c) Archive data on tape for later recall without reanalysis.

5. Collection of data from multiple field units by storing data from a particular field unit when polling the field unit via the modem. Preferably the time report sequence of the field units would be preprogrammed into the control apparatus 22 during the calibration mode.

In order to provide the above specified functions, the system scanner 30 will require additional peripheral equipment in addition to the personal computer 32. The personal computer 32 will preferably include adequate memory, for example 64K to 256K, a keyboard 100 and a high resolution graphics CRT 102. In the preferred embodiment shown, two disk drives 104 are also utilized, however, one may be sufficient for lower use installations. A modem 106 positioned either internally of the computer or externally as shown in FIG. 3, will be required at the central site to provide communications with the modem 28 at the remote site. As illustrated in FIG. 3, the modems 28 and 106 typically will be interconnected either directly or acoustically to telephone sets, illustrated by reference numerals 29 and 107. The telephone sets 29 and 107 will, in turn, typically be interconnected by a conventional voice grade telephone-line 118. In addition, if the remote site utilizes the tape deck 34 or data transfer, a corresponding tape deck 108 will be required at the central site. For hard copy or print out purposes, a printer and/or plotter 110 will be required. Corresponding RS232C interface capabilities will preferably be utilized for the tape deck 108 and the printer and/or plotter 110 interfaces. Additionally, a parallel interface capability might be present for future enhancements of the system scanner. The various hardware elements of the system scanner might have disk desk top configuration optimized for minimal area occupancy.

In addition to the hardware requirements, the software will include appropriate operating system software, various utility software such as tape, modem, multiplexer mode, plotter, and CRT dump capability, and various interface software providing for calibration, downloading and direct hookup of the nocturnal penile and tumescence rigidity monitor to the computer 32 to enable real time data transfer for real time functional verification of the tumescence and rigidity monitor. In addition, software providing for data analysis and number crunching will also be required. For output purposes, 2D and 3D graphic software may be required as well as report form generation software enabling patient data, session data and graphic summaries for hard copy patient reporting. In addition, it is preferred that there be interactive user operation of software for menu selected CRT graphics, data analysis options and printout. As a further support measure, it is preferred that the software also provide for patient file bookkeeping, enabling the patient's files to be updated.

One possible alternate embodiment of the present invention is the use of a chart recorder in place of or in addition to the system scanner. The chart recorder will include an analog chart recorder or a dot matrix printer preferably utilizing standard sized paper. Either a serial RS232C interface (if digital) or an analog specified interface (if analog) to the nocturnal penile tumescence rigidity monitor apparatus will be provided for interconnection of the chart recorder to the potentiometer output of the monitor apparatus. Accordingly, the chart recorded will be capable of providing a hard copy of the tumescence data in the real time or at the completion of a session. The chart recorder will preferably be capable of multichannel operation. While the chart recorder as currently envisioned will provide only 2D graphics capability, it will be of minimal size enhancing portability.

Typically, use of the nocturnal penile tumescence and rigidity monitor apparatus will include a scenario having the following phases of operation:
   1. Patient introduction and monitor initiation.
   2. Patient monitoring session.
   3. Transfer of session data.
   4. Data analysis and reporting.

Prior to patient introduction to the monitor apparatus, the control apparatus 22 battery is charged and the monitor apparatus is interconnected to the system scanner 30 for initialization to enter the patient's name, I.D. number, date/time, modem dial time for automatic reporting, and modem serial number. This information is entered via the keyboard 100. The initialization information is also stored in the scanner disk patient file for recall and recombination with the collected session data. From this point on, the monitor apparatus need not be attached to the system scanner 30. The patient is introduced to the monitor apparatus by demonstrating monitor calibration and operation. Monitor calibration is performed by placing the monitor loops 38 around a built-in calibration cylinder and pressing a calibration function key 112 on the housing 42 of the monitor apparatus. Upon pressing the calibration function key 112, the monitor apparatus will take a tumescence and rigidity sample. Force/displacement constants are derived based on the known force applied and the known rigidity of the calibration cylinder. The constants are then stored internally for the force displacement transfer function for determining tumescence and rigidity. The monitor loops 38 are then placed around the patient's penis for finger printing. When the calibrate function key is again pressed, the monitor will take a tumescence and rigidity sample which is stored and identified as a finger print of that patient's characteristics. The monitor will continue to sample once a minute until the stop function key 114 on the housing 42 is pressed at which time the monitor will shut itself off. (The calibration function key 112 initiates the monitoring functions while the stop function key 114 terminates the functions.) This exercise serves a two-fold purpose; patient instruction and security for maintaining patient integrity. The monitor is then detached and given to the patient for home use over a predetermined length of time, e.g. one to five nights of recording.

The patient will calibrate, attach and wear the monitor for consecutive nights until the necessary data is collected. Singular nocturnal session data may be downloaded to tape or to modem daily by simply connecting the monitor to the peripheral box 24 containing the tape deck 34, modem 28 and the AC adapter/charger 26 on awakening. This will transfer the data collected and recharge the monitor's battery. Session disruption or patient notations can be made with a patient activated event marker function key 116 on the housing 42. Upon pressing the event marker function key 116, the date and time is recorded. The patient should then record in a separate log or diary, the reason for the session disruption. This will facilitate interpretation of the data upon being returned to the clinic or other central site. Should the battery be weak or dead, the monitor may be connected to the peripheral box via a suitable cord connector. While the unit is no longer ambulatory at this point, this is not expected to be the normal operating procedure and should be avoided when possible.

After having collected the data, the data is transferred to the central system scanner 30. The monitor apparatus provides flexibility of getting acquired data to the central site (clinic or hospital) in a convenient manner without impacting the "ambulatory" nature of the device. Following are three data transfer possibilities for the nocturnal penile tumescence and rigidity monitor.

One is the traditional cassette tape transfer which is proven reliable but somewhat clumsy. The problem is the size of the tape transport; it greatly increases the ambulatory monitor's size. It also requires more battery backup (even though it isn't "on" that often in the course of monitor session), and that increases battery size and weight. So its integration into the ambulatory monitor for data storage is unlikely if the monitor is to remain "ambulatory" in the true sense of the word (which implies light weight, small and comfortable). The tape deck 34 will be housed in peripheral housing 24 with the battery charger/AC adapter and modem. This configuration requires daily downloading of the monitor data on tape in final archival form. The tape, represented by reference numeral 35, would then be handcarried to the system scanner 30. The monitor needs provisions for only one session of data storage. However, if semiconductor storage density is utilized (such as with 2K×8 or 8K×8 bit CMOS Static RAM IC's) in the unit itself sufficient for 3 monitor sessions, the peripheral box 24 may only be necessary for power support, and data would transfer inherently with return of the monitor to the central site and then be down loaded directly into the system scanner 30.

The second transfer option is the use of the modem 28, or modulator-demodulator for telephone data communications. The modem, because of size, may also be required to reside in the peripheral box 24 with the tape deck 34 and the adapter/charger 26. Its support would be to provide daily update to the clinic of patient data and operational verification of the monitor. This role may eliminate the need for field tape support. The data would be archived on tape or disk at the central site. The patient would connect the monitor to the peripheral box 24 at the conclusion of the monitor session. Preferably, auto modem control would take over for the whole reporting process.

The third transfer option downloads the data from the monitor to the system scanner 30 via direct connection. This is possible when all sessions are recorded using suitable memory such as solid-state or bubble memory, or when the recording sessions are conducted in close proximity to the scanner site.

Once data is resident in the system scanner 30, analysis may begin. Penile tumescence and rigidity data, patient data, date/time, etc., is analyzed and coordinated to present the final hard copy report. Data is analyzed, formatted and archived on suitable mass storage such as cassette tape for future recall if necessary. The final report might consist of a hard copy of any or all of the following information:

(a) patient data—name, ID number;
(b) date/time;
(c) monitor serial number;
(d) "finger print" samples of tumescence and rigidity;
(e) Initialized Thresholds—preset constants in the data analysis equations which may be altered for appropriate reason;
(f) Session Summary—numerical data summary of nocturnal penile tumescence and rigidity events, e.g. max, min, total time, etc., patient activation notations and verbal description of patient;
(g) 2-D Graphics—superimposition of all or any number of data including tumescence and rigidity versus time plots for the tip and base loop portions which might be displayed in two forms, entire session data and individual event data; and,
(h) 3-D Graphics—optional 3-D graphics of entire session or individual events data which are plots of tumescence vs. rigidity vs. time.

It is to be understood, however, that even though numerous characteristics and advantages of the invention have been set forth in the foregoing description, together with details of the structure and function of the invention the disclosure is illustrative only, and changes may be made in detail, especially in matters of shape, size and arrangement of parts within the principles of the invention, to the full extent indicated by the broad general meaning of the terms in which the appended claims are expressed.

What is claimed is:
1. A penile rigidity and tumescence monitor apparatus, comprising:
  (a) transducer means for providing output signals indicative of penile rigidity and tumescence throughout a penile tumescence event; and,
  (b) control means operatively interconnected to said transducer means for providing control of said transducer means, said control means further providing for acquisition of said out put signals.

2. A monitor apparatus in accordance with claim 1, wherein said control means includes interface means for providing communication with peripheral equipment.

3. A monitor apparatus in accordance with claim 1, wherein said control means, in cooperation with said transducer means, further includes means for recording of penile rigidity and tumescence data throughout the penile tumescent event.

4. A monitor apparatus in accordance with claim 3, wherein said control means includes means for recording the penile data at predetermined intervals.

5. A monitor apparatus in accordance with claim 3, wherein said monitor apparatus further includes means for interfacing with programmable means providing for analysis of the penile rigidity and tumescence data.

6. A monitor apparatus in accordance with claim 5, wherein said programmable means in cooperation with suitable printer means provides for hard copy printout of the penile rigidity and tumescence data.

7. A penile rigidity and tumescence monitor apparatus, comprising:
(a) a portable housing;
(b) an elongated, non-distensible, flexible member extending from said housing, said elongated member constructed and arranged for forming a loop-like portion at a first end, said loop-like portion adapted for releasably encircling a penis about the circumference thereof, said elongated member being slideably enclosed within a flexible non-compressible conduit between said loop-like portion and said housing, said non-compressible conduit being fixedly attached to said housing, said elongated member further being slideably enclosed in a collapsible, soft sheath along said loop-like portion;
(c) tension means positioned within said housing and operatively interconnected to said elongated member for placing said elongated member in a tensioned condition, whereby changes in the penile circumference result in a longitudinal displacement of said elongated member with respect to said conduit;
(d) sensing means operatively interconnected to said elongated member for sensing displacement of said elongated member with respect to said conduit in response to changes in penile circumference, said sensing means providing output signals indicative of said changes in penile circumference;
(e) means operatively interconnected to said elongated member for exerting a predetermined force on said elongated member, said force means tending to reduce the circumference of the loop-like portion and correspondingly the penis at the location to which it is attached, said sensing means sensing displacement of said elongated member as a result of said predetermined force applied by said force means and providing an output signal indicative of changes in the penile circumference; and,
(f) control means for providing control of the monitor apparatus.

8. A monitor apparatus in accordance with claim 7, wherein said elongated member and said tension means are operatively interconnected to a sprocket and chain drive means.

9. A monitor apparatus in accordance with claim 8, wherein said predetermined force means includes drive motor means operatively interconnected to said sprocket and chain drive means for driving said sprocket and chain drive means.

10. A monitor apparatus in accordance with claim 9, wherein said sensing means includes a potentiometer operatively interconnected to said sprocket and chain drive means.

11. A monitor apparatus in accordance with claim 10, wherein said tension means includes a constant force spring interconnected to said sprocket and chain drive means.

12. A monitor apparatus in accordance with claim 7, wherein said predetermined force means includes means for exerting a predetermined force at predetermined intervals.

13. A monitor apparatus in accordance with claim 7, wherein said control means includes programmable means providing activation of said force means according to a preprogrammed algorithm.

14. A monitor apparatus in accordance with claim 13, wherein said control means includes means for activating said force means more frequently during a penile tumescence event than during penile inactivity.

15. A penile tumescence monitor apparatus, comprising:
(a) transducer means providing output signals indicative of penile tumescence, said transducer means including an elongated member slideably enclosed within a non-compressible sheath along a portion thereof, said elongated member being adapted for forming a loop portion for releasable attachment about the circumference of a penis, said elongated member being slideably displaced within said sheath due to changes in penile circumference, said transducer means including means for placing said elongated member in a tensioned condition, said transducer means also including means operatively interconnected to said elongated member for monitoring the displacement of said elongated member due to changes in penile circumference; and,
(b) control means operatively interconnected to said transducer means for providing control of said transducer means.

16. A monitor apparatus in accordance with claim 15, said monitor apparatus includes means for exerting a predetermined force on said elongated member tending to reduce the size of said loop-like portion and cause slideable displacement of said elongated member in said sheath, whereby penile rigidity can be determined from the change in circumference due to application of said predetermined force.

17. A monitor apparatus in accordance with claim 16, wherein said control means includes a programmed processor means which provides for activation of said force means at predetermined intervals.

18. A monitor apparatus in accordance with claim 17, wherein said programmed processor means includes means for sampling the transducer signal at different rates depending on the degree of tumescence.

19. A method of monitoring penile tumescence and rigidity, comprising the steps of:
(a) placing an expandable loop around the circumference of a penis in such a way that penile tumescence is reflected in changes in the circumference of the loop;
(b) measuring the circumference of the loop at predetermined intervals;
(c) storing the circumference measurement if the current measurement is different than the measurement at the previous interval by a first predetermined amount, whereby a record of tumescence is stored;

(d) reducing the circumference of the loop under a predetermined force if the current measurement is different than the measurement at the previous interval by a second predetermined amount; and, (e) measuring the change in circumference of said loop due to the application of said predetermined force, and utilizing said change as an indication of rigidity.

* * * * *

UNITED STATES PATENT AND TRADEMARK OFFICE
CERTIFICATE OF CORRECTION

PATENT NO. : 4,515,166

DATED : May 7, 1985

INVENTOR(S) : Gerald W. Timm

It is certified that error appears in the above-identified patent and that said Letters Patent is hereby corrected as shown below:

Please change the title of this patent to read as follows:
--NOCTURNAL PENILE TUMESCENCE AND RIGIDITY MONITOR AND METHOD--.

Col. 1, line 12, delete "tumescence" and insert --tumescent--.

Col. 2, line 1, delete "or" and insert --of--.

Col. 2, line 31, delete "tumescent" and insert --tumescence--.

Col. 2, line 39, delete "physicians" and insert --physicians'--.

Col. 2, line 49, delete "is" and insert --are--.

Col. 2, line 52, delete "tumescence" and insert --tumescent--.

Col. 2, lines 57-58, delete "tumescence" and insert --tumescent--.

Col. 2, line 60, delete "included" and insert --include--.

Col. 3, line 35, delete "tumescent" and insert --tumescence--.

Col. 5, line 9, delete "diagramatic" and insert --diagrammatic--.

Col. 5, line 13, delete "diagramatic" and insert --diagrammatic--.

Col. 5, lines 19-20, delete "diagramatically" and insert --diagrammatically--.

Col. 5, line 53, delete "connect" and insert --connection--.

Col. 5, line 62, delete "non compressible" and insert --non-compressible--.

Col. 6, line 59, delete "tension" and insert --tensioned--.

Col. 6, line 60, delete "principals" and insert --principles--.

Col. 6, line 66, delete" elogated" and insert --elongated--.

Col. 6, line 67, delete "placed" and insert --place the--.

UNITED STATES PATENT AND TRADEMARK OFFICE
CERTIFICATE OF CORRECTION

PATENT NO. : 4,515,166

DATED : May 7, 1985

INVENTOR(S) : Gerald. W. Timm

It is certified that error appears in the above-identified patent and that said Letters Patent is hereby corrected as shown below:

Col. 7, line 5, delete "principals" and insert --principles--.

Col. 7, line 10, delete "on" and insert --of--.

Col. 7, lines 20-21, delete "principals" and insert --principles--.

Col. 7, line 54, delete "tumescence" and insert --tumescent--.

Col. 9, line 66, delete "disk" and insert --a--.

Col. 10, line 31, delete "recorded" and insert --recorder--.

Col. 11, line 44, after "which" delete "is" and insert --has--.

Col. 11, lines 66-67, delete "down loaded" and insert --down-loaded--.

Col. 12, line 14, delete "downloads" and insert --down-loads--.

Signed and Sealed this

Thirtieth Day of September 1986

[SEAL]

Attest:

DONALD J. QUIGG

Attesting Officer

Commissioner of Patents and Trademarks